United States Patent
Sundström et al.

(10) Patent No.: US 8,109,899 B2
(45) Date of Patent: Feb. 7, 2012

(54) FULLY AUTOMATED METHOD OF MEASURING AND REGULATING CEREBROSPINAL FLUID PARAMETERS USING DISPOSABLE TUBE-SET

(75) Inventors: Nina Sundström, Umeå (SE); Kjell Öberg, Umeå (SE)

(73) Assignee: Likvor AB, Umeå (SE)

( * ) Notice: Subject to any disclaimer, the term of this patent is extended or adjusted under 35 U.S.C. 154(b) by 31 days.

(21) Appl. No.: 12/803,685

(22) Filed: Jul. 2, 2010

(65) Prior Publication Data

US 2011/0021991 A1    Jan. 27, 2011

Related U.S. Application Data (60) Provisional application No. 61/270,331, filed on Jul. 6, 2009.

(51) Int. Cl.
*A61M 31/00* (2006.01)
*G01M 3/02* (2006.01)
*A61B 5/00* (2006.01)
*A61M 1/00* (2006.01)

(52) U.S. Cl. .............. 604/66; 604/8; 604/9; 604/65; 604/67; 604/151; 604/153; 73/37; 600/561

(58) Field of Classification Search ........... 604/8–10, 604/30, 31–153; 600/561, 587, 594, 309, 600/366; 73/37, 861, 861.44, 861.45
See application file for complete search history.

(56) References Cited

U.S. PATENT DOCUMENTS

| | | | |
|---|---|---|---|
| 4,114,603 A | | 9/1978 | Wilkinson |
| 4,598,579 A | * | 7/1986 | Cummings et al. .......... 73/37 |
| 6,531,061 B1 | | 3/2003 | Cholewa |
| 6,731,976 B2 | | 5/2004 | Penn et al. |
| 2005/0187509 A1 | | 8/2005 | Wolf |
| 2006/0020239 A1 | | 1/2006 | Geiger et al. |
| 2007/0217933 A1 | | 9/2007 | Haser et al. |

FOREIGN PATENT DOCUMENTS

| | | |
|---|---|---|
| EP | 1 676 527 A1 | 7/2006 |
| EP | 1 749 549 A1 | 2/2007 |
| EP | 2 008 683 A1 | 12/2008 |
| JP | 11299742 | 11/1999 |
| JP | 3052238 | 12/2000 |
| WO | WO 02/03860 A1 | 1/2002 |
| WO | WO 2006/091164 * | 8/2006 |
| WO | WO 2006/091164 A1 | 8/2006 |
| WO | WO 2006/091581 A1 | 8/2006 |

* cited by examiner

*Primary Examiner* — Nicholas Lucchesi
*Assistant Examiner* — Leah Stohr
(74) *Attorney, Agent, or Firm* — Lynn E. Barber (57) ABSTRACT

A method and device for measuring and regulating pressure and flow in the spinal canal, in order to characterize individual patient's cerebrospinal fluid (CSF) dynamics. A unique disposable tube-set plate, with computer regulated automated solenoids is used to control flow pressure and the location of a small pressure sensor allows for fully automatic control of the analysis process.

11 Claims, 5 Drawing Sheets

FULLY AUTOMATED METHOD OF MEASURING AND REGULATING CEREBROSPINAL FLUID PARAMETERS USING DISPOSABLE TUBE-SET

CROSS-REFERENCE TO RELATED APPLICATIONS

This application claims priority from U.S. Provisional Application Ser. No. 61/270,331 filed Jul. 6, 2009.

BACKGROUND OF THE INVENTION

1. Field of the Invention

The present invention relates to the use of a new automated method which measures and regulates pressure and flow in the spinal canal in order to characterize individual patients' cerebrospinal fluid (CSF) dynamics. To accomplish this, a unique disposable tube-set plate with computer regulated solenoid pinch valves to control flow pressure and a new location of small pressure sensors allows for fully automatic control of the system.

2. Description of the Related Art

Hydrocephalus is a condition affecting people who are unable to properly regulate their cerebrospinal fluid circulation. Cerebrospinal fluid (CSF) produced by the ventricular system is normally absorbed by the venous system. In a person suffering from hydrocephalus, the cerebrospinal fluid is not absorbed in this manner, but instead accumulates in the ventricles (free spaces) of the patient's brain. Normal pressure hydrocephalus (NPH) refers to a condition of pathologically enlarged ventricular size with normal pressures on lumbar puncture. If left untreated, an increasing volume of fluid can elevate the patient's intracranial pressure and can lead to serious medical conditions such as compression of the brain tissue and impaired blood flow to the brain.

The earliest description of hydrocephalus has been ascribed to Hippocrates (466-377 BC), who pointed out symptoms such as headache, vomiting and visual disturbance. Claudius Galen of Pergamon (130-200 AD) and medieval Arabian physicians also described hydrocephalus, believed to be due to an extracerebral accumulation of water.

Surgery to reduce fluid accumulation in the cerebrospinal fluid system was first performed by Le Cat in 1744, but it was not until the late nineteenth century, when sufficient pathophysiological knowledge and aseptic conditions were gained, that surgical procedures were truly introduced to treat hydrocephalus. In the 1960s, silicone and the invention of artificial valves led to a therapeutic breakthrough. With the development of an implantable shunt system to divert excess fluid, hydrocephalus went from being a fatal disease to becoming curable (Aschoff A, et al. The scientific history of hydrocephalus and its treatment. Neurosurg Rev 22:67-93; discussion 94-5, 1999). In 1965, Hakim and Adams described the newly discovered category of patients with normal cerebrospinal fluid pressure appearing to suffer from hydrocephalus, who benefited from shunt surgery (Hakim S and Adams R D. The special clinical problem of symptomatic hydrocephalus with normal cerebrospinal fluid pressure. Observations on cerebrospinal fluid hydrodynamics. J Neurol Sci 2:307-27, 1965). The syndrome was named normal pressure hydrocephalus (NPH), and since then extensive work has been put into finding and developing new methods to identify those patients with NPH who will improve from shunt implantation surgery. Today, ventricular shunting is one of the most commonly performed neurosurgical procedures, including for communicating and non-communicating hydrocephalus as well as shunt malformation. The annual incidence of operations varied between regional clinics from 2.3 to 6.3 per 100,000 inhabitants (Tisell M, et al. National and regional incidence of surgery for adult hydrocephalus in Sweden. Acta Neurol Scand 2005 August; 112(2):72-5).

Shunting has dramatically changed the prognosis of people with hydrocephalus, many of them benefiting from normal life expectancies and regaining their baseline intelligence. The use of shunts, however, has created many unique problems of shunt dependence with frequent shunt revisions being the rule for most hydrocephalic patients. Shunt complications assume a major amount of all neurosurgeons' efforts.

CSF shunt implantation surgery involves establishing an accessory pathway for the flow of CSF in order to bypass an obstruction of the natural pathways. The shunt is positioned to enable the CSF to be drained from the cerebral ventricles or subarachnoid spaces into another absorption site, such as the right atrium of the heart or the peritoneal cavity, via a system of small tubes known as catheters. A regulatory device (known as a valve) can be inserted into the pathway of the catheters in order to regulate flow of CSF, depending on the pressure. This drainage enables the excess CSF within the brain to be evacuated and thereby, the pressure within the cranium to be reduced.

The currently accepted means of measuring pressure and flow dynamics of CSF is a two-part clinical exam, known as the lumbar infusion test and CSF tap test. These tests are limited in that they do not allow for standardization for the measurement and regulation of pressure and flow of CSF, and require manual adjustment throughout the examination. The infusion test investigates the dynamics of the CSF system, and since the shunt treatment of IAHS involves imposing a change on the CSF dynamical system, it is natural to look at the function of the system before treatment. The infusion test determines the patient's intracranial pressure (ICP) at rest, and the conductance to CSF outflow ($C_{out}$, inverse of outflow resistance, $R_{out}$). The infusion test can also be used to determine shunt function in patients on whom there has already been an operation. A problem with the infusion test is that it is carried out, analyzed and interpreted in different ways at different investigating centers. Some of the most common methods used to determine $C_{out}$ (or $R_{out}$) include Katzman's constant rate infusion test with various modifications, the bolus injection and servo-controlled constant pressure infusion. Although the bolus test is known to produce a higher $C_{out}$ than the other methods they all claim clinical utility but with different $C_{out}$ threshold levels. There is a lack of consensus concerning the usefulness of $C_{out}$ as a predictor for shunt surgery, with a large number of studies supporting it but many as well not finding the parameter useful in the selection process A challenge with this type of measurement is that the physiological periodic variations in ICP, related to vasogenic volume variations in the craniospinal system, often are large and the net infusion flow is small. This can be viewed as a low signal to noise ratio. Also, the magnitude of the variations differs greatly between patients. This will affect each individual infusion test in such a way that the results obtained from a patient with small variations, will be more reliable than those from a patient with larger variations. None of the methods currently in use for performing infusion tests give any numerical feedback, on a display or in printout form or the like, to the user concerning the reliability of individual investigations. Consequently, all $C_{out}$ values are considered equally reliable, regardless of their physiological background. Based on such data the analysis and the interpretation of individual $C_{out}$ values are difficult, and the lack of consensus concerning the usefulness of $C_{out}$ as a predictor might be a consequence of the unknown uncertainty of individual infusion tests. One of the major benefits of the automated tube-set invention herein is the flexibility of the system, in that the user can combine these different components (constant pressure, constant flow, or bolus injection) to attain the desired measurement.

Using the prior machine invention (WO 2006/091164), which systematically generates or provides pressure and flow information, the hydrodynamic parameters of a patient are determined in order to confirm diagnosis of hydrocephalus. In particular, this prior machine for determining the hydrodynamic properties of the fluid system surrounding the brain and the spinal cord comprises a hose pump for infusion of artificial cerebrospinal fluid for example Ringer's acetate, a pump hose, pressure transducers for continuous registration of the intracranial pressure, an invasive contact object for creating fluid contact with the cerebrospinal fluid system and a computer with software for computerized collection and analysis as well as control of pump speed, characterized in that a calculation unit, forming part of said software, is designed to be controlled thereby using an adaptive method which at each pressure-flow level considers the time of measure and the patients fluctuations in physiologic signals for calculating, in real time, when the relation between measure time and measure accuracy in pressure and flow on the actual level is sufficient, that said software is designed for, when said relation between measure time and measure accuracy on the actual level is sufficient, initiating the next pressure-flow level according to a predetermined protocol, and that for real-time analysis, said software is designed for, from the pressure-flow information from the investigation, determining and giving an account of the patient's hydrodynamic parameters with an uncertainty estimate. In conjunction with this machine, a new disposable and fully automated tube-set of the invention herein, can be used for more accurate, simple, fully automatic, and sterile measurements of the pressure and flow dynamics of CSF.

The earlier version of the apparatus mentioned above, for performing standardized and semi-automated infusion tests was developed by Sundström in WO 2006/091164. The apparatus was PC-based with a user interface consisting of a computer screen and a track ball (see FIG. 1 of WO 2006/091164). It also included an electronic control unit, two pressure transducers (PMSET 1TNF-R, BD Critical Care Systems Pte Ltd, Singapore), a peristaltic pump (Reglo-Analog-E, MS/CA1-E/12-160, Ismatec, Switzerland), a bottle holder for artificial CSF, an emergency stop and a set of tubing. Data collection and communication between software and hardware were performed using two data acquisition cards, PCI-MIO-16XE-50 and PCI-6503 (National Instruments, Inc., Austin, Tex., USA). The electronic control unit included pressure amplifiers, analogue safety checks that stop the pump at dangerously high or low ICP, and a signal to ensure communication with the PC. A built-in horizontal laser line was used for zero level alignment of the equipment in relation to the patient. The components were mounted on an electrically maneuvered pillar and the pillar was mounted on wheels to make the system mobile.

The use of the invention herein, the automated tube-set, improves prior methods of gathering these measurements. Previously, pressure flow levels were set manually in the beginning and at the end of the examination period via eight adjustable valves. Instead of using manually adjustable stopcocks of the semi-automated system, the invention herein has automatic magnetic solenoid pinch valves that are regulated using computer software. This means that the automated tube-set is not subject to operator variability and thus the invention herein is safer for the patient than previous methods. This renders the entire analysis process of measuring pressure and flow dynamics of CSF automatic.

The invention herein is much easier and faster for the operator to mount than prior methods. With the previous tube-set, the user had to know how to connect approximately eight different parts, while in the present invention, the plate needs only to be snapped on to the instrument for mounting.

In addition, the time needed to acquire exact measurements has not been known or standardized in prior techniques, whereas the automated tube-set eliminates this variable by adjusting automatically to the patient from the beginning to the end of the exam. Another advantage of the automated tube-set technology herein is that people of various training levels can use it, since it is a fully automated method. This improves simplicity and thereby, accuracy of the results. At the same time, accuracy and simplicity also improve with a closer sensor location to the tube and the patient, without the need to draw fluid into the machine. The unit is also disposable, which means it is easy to keep sterile and safe for each individual patient. The location of a new and smaller pressure sensor directly on the disposable tube-set also improves issues of sterility.

Similar technology i.e. a tube-set on a plate or cassette is found in peristaltic pump devices, which have been widely used for life support during open-heart surgery and dialysis over the last few decades. In a peristaltic pump, a piece of tubing is compressed in a forward motion with the tube acting both as a check valve and as a transport mechanism. A peristaltic pump is used principally for pumping blood products. Typically, a peristaltic pump has a rotor with two rollers, which squeeze the tube up against a circular tube track. The tube-set plate of the invention herein differs from the earlier tube-set technology in for example, that the tube-set of the invention is regulated by automatic valves that open and close according to pressure flow parameters. The pressure flow translates the pressure of the CSF into an electronic signal, which yields a measurement of the results.

In U.S. Pat. No. 6,531,061, a dialysis cassette is assembled by the combination of a first and second flexible polymeric sheet bonded together to form a semi-rigid frame. It is a disposable dialysis cassette that is flat, flexible, self-closing and applicable to solutions containing proteins, DNA, RNA, or other molecules. The dialysis cassette embodies a first and second semi-permeable dialysis membrane, or tubular dialysis membrane, sealed by a flexible frame to form a dialysis chamber having a self-closing channel for the introduction of a dialysis sample by either a pipette or other dispensing mechanism. However, this system does not open automatically as the invention herein, and functions on an osmotic gradient rather than a pressure flow parameter.

In U.S. Patent Publication No. 2007/0217933, for a tubing cassette for a peristaltic pump, a hose cartridge is provided for a peristaltic pump comprising a cartridge housing, including a flexible pump hose segment extending through the cartridge housing. Both ends of the pump hose segment are fixed in the cartridge housing by means of a first fixing member and of a second fixing member arranged in the area of a first front face of the cartridge housing. The cartridge housing comprises a recess for the engagement of a roller wheel of the pump in the interior of the cartridge housing. In this case, the fluid is transported via the hose pump, rather than the automated pressure flow parameters of the patient as described by the invention herein.

It is an object of the invention to provide an improved and simplified method of fully automating the measurement of CSF pressure and flow dynamics by using a disposable tube-set plate. Other objects and advantages will be more fully apparent from the following disclosure.

SUMMARY OF THE INVENTION

The present invention provides a new automated method and device to measure and regulate pressure and flow in the spinal canal, in order to characterize an individual patient's cerebrospinal fluid (CSF) dynamics. To accomplish this, a unique disposable tube-set plate, with computer regulated solenoid pinch valves to control fluid pressure and a new location of a small pressure sensor, allows for full automatic control of the analysis process. Other than this invention, herein called CELDA™ Tools, there is no known fully automated method comparable to this technique.

DETAILED DESCRIPTION OF THE INVENTION AND PREFERRED EMBODIMENTS THEREOF

The invention herein describes a new method for automating the measurement of pressure and flow dynamics of CSF. Specifically, the CELDA™ Tools of the invention herein consists of a single-use sterile tube-set that is attached to the front of the instrument housing on the CELDA™ unit. The CELDA™ unit, in addition to the tube-set includes the complete instrument including electronics, pumps, software etc. The software used herein is adjusted from the previous software as known in the art to accomplish the method of the invention.

Figure 1:
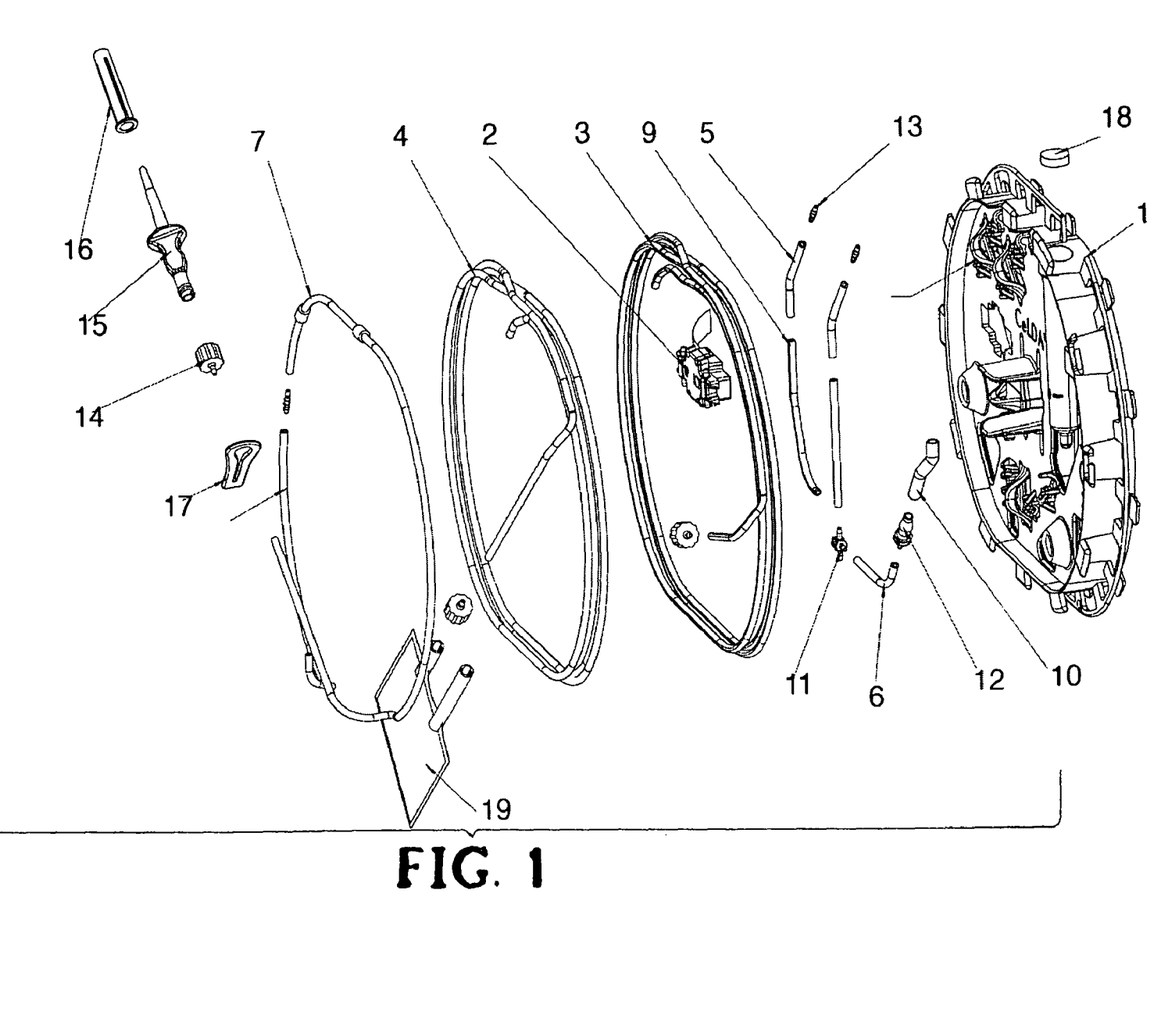
FIG. 1 is an expanded view of the tube-set plate of the invention herein
Figure 2A:
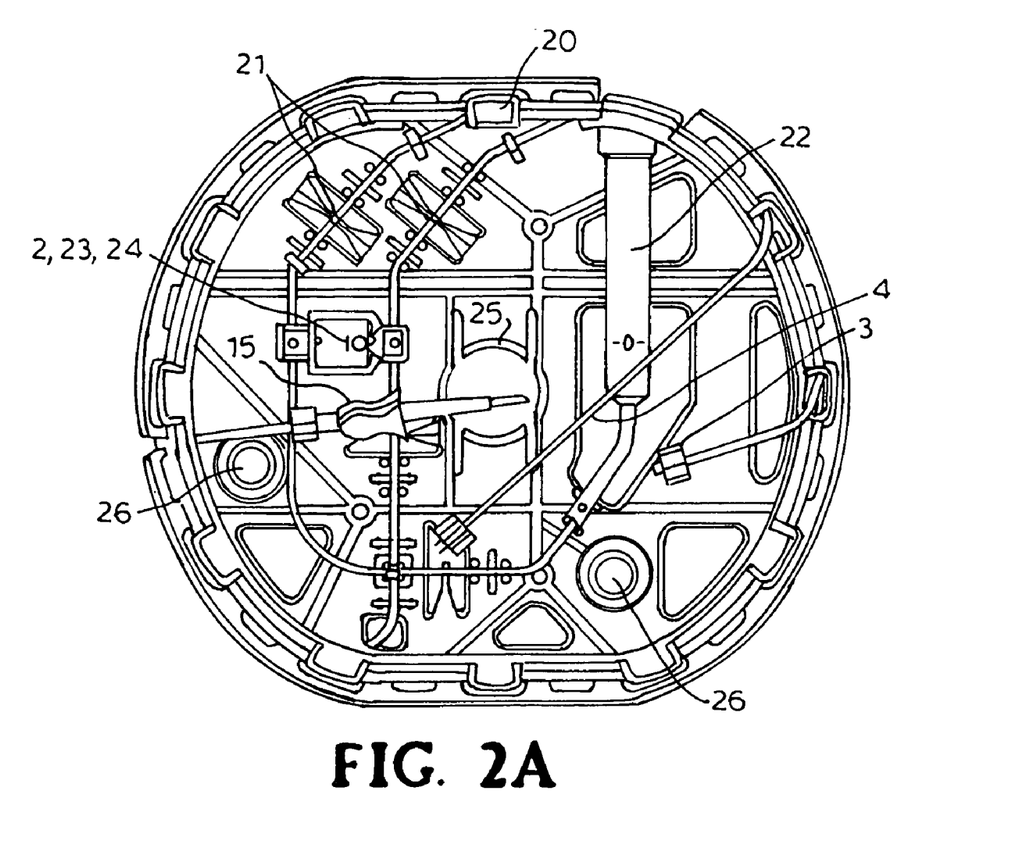
FIGS. 2a and 2b show views from front and from the back of the tube-set plate of the invention herein
Figure 2B:
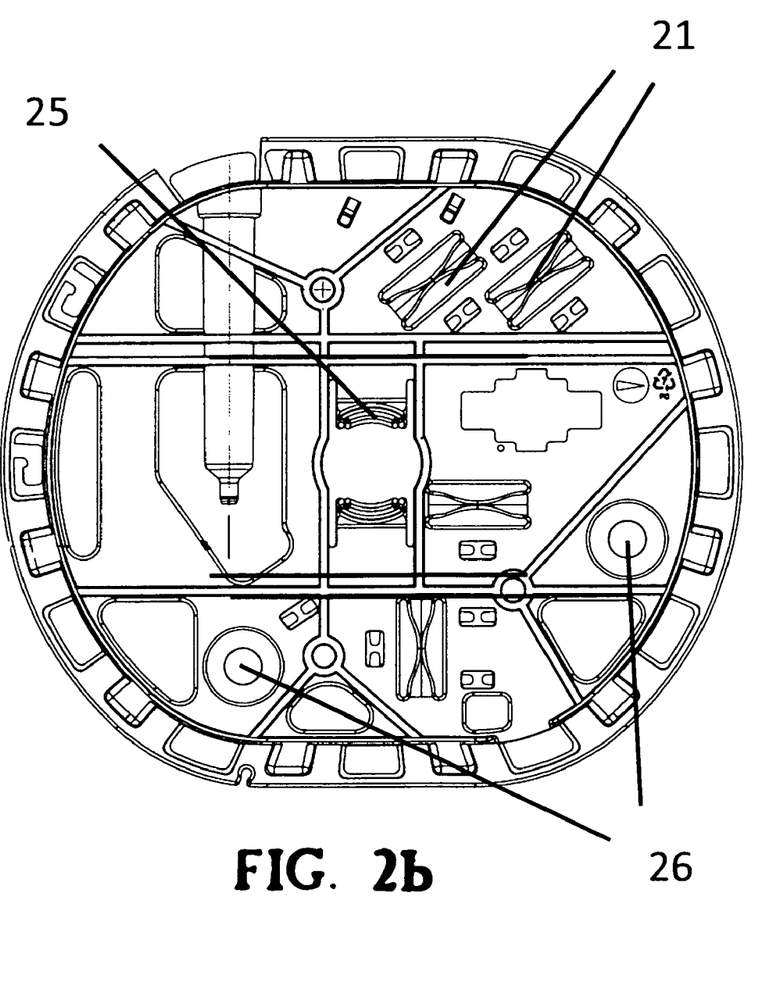

As shown in FIGS. 1-2, the tube-set consists of a polycarbonate disposable plate 1 that is attached to the front of the instrument housing, pump tube 7, two pressure sensors 23,24, pressure calibration tube 22, linking tubes, patient tubes 3,4 and a 30 mL liquid container 19 at the distal ends of the patient tubes.

Components of the invention herein, and where applicable, possible providers thereof, preferably include the following
1. disposable (plastic-molded) base plate,
2. pressure sensor housing of molded plastic,
3. patient IP tube (Optima AB, Gunstagatan 16, SE-753 24, Uppsala, Sweden);
4. patient ICP tube (Optima);
5. pinch tube (Raumedic AG, Hermann-Staudinger-Straße 2, 95233 Helmbrechts, Germany
6. pinch tube (Raumedic),
7. pump tube (Raumedic),
8. pump tube extension (Optima),
9. IP-tube extension (Optima),
10. calibration tube connection (Raumedic),
11. four-part cross (Value Plastics Inc., 3325 South Timberline Rd., Fort Collins, Colo. 80525, USA),
12. straight through reduction connector (Value Plastics),
13. straight through connector (Value Plastics),
14. male luer lock to barb connector (Qosina Inc., 150-Q Executive Drive, Edgewood, N.Y. 11717-8329 USA),
15. non-vented spike with female luer lock (Qosina),
16. vented cap (Qosina),
17. slide clamp (Qosina),
18. porous plug (Porex Inc., 500 Bohannon Road, Fairburn, Ga. 30213-4747, USA),
19. liquid container (Specialplast AB, Gillinge, 186 91 Vallentuna, Sweden),
20. tube-securing sleeve,
21. solenoid pinch valves (Raumedic),
22. pressure calibration tube (Raumedic),
23, 24. pressure sensors (Freescale Inc., 6501 William Cannon Drive West, Austin, Tex. 78735, USA
25. central conical bayonet fitting (plastic-molded)
26. holes in the plate for guiding pins
27. guiding pins on instrument
28. solenoid cock
29. pressure sensors socket
30. peristaltic pump
31. emergency stop This invention relates to a method and device for measuring and regulating pressure and flow in the spinal canal, in order to characterize individual patients' cerebrospinal fluid (CSF) dynamics. To accomplish this, a unique disposable tube-set plate, with computer regulated automated solenoids to control flow pressure and a location of a pressure sensor as close as possible to the patient allows for full automatic control of the analysis process with a higher precision than previous solutions.

Example 1

Mounting the Tube-Set

To mount the tube-set of the invention herein, CELDA™ tools, the operator opens its packaging and removes the protective film from the pressure sensor housing 2. The tube-set then easily clips on to the instrument of patent WO 2006/091164 using a central conical bayonet fitting 25. The tube-set also has two holes 26 which guide pins on the instrument, now fitted with guiding pins on the instrument 27 and a bayonet fitting 25 to assure a correct mounting on the instrument, preventing the tube-set from rotating out of place. The pump tube 7 is then unwound and mounted on a peristaltic pump on the instrument. The spike at the end of the pump tube 7 inserts into a Ringer's acetate bag (not shown) hanging on one side of the instrument.

Example 2

Priming

The operator starts with the instrument, which undergoes a self-test procedure, and then automatically primes the tube-set. The purpose of the priming is to fill the tubes with Ringer's acetate. The pump runs continuously and the software automatically regulates the solenoid pinch valves to direct the flow to the different tubes, Patient IP (infusion pressure) and the Patient ICP (intracranial pressure) tubes 3,4, which fill one by one. At the end of the tubes, a small custom-made bag, liquid container 19 is attached to prevent any spillage from the priming. The last step of the priming consists of pumping liquid to a specific level in a pressure calibration tube 22. This pressure calibration tube 22 is also an integrated part of CELDA™ tools. The level is marked with a line so that the operator can easily see if the level is correct. When the automatic process is finished; the operator is given the opportunity to manually control the valves and the pump to remove any residual air bubbles, or to finely adjust the level in the pressure calibration tube 22.

Example 3

Application in a Patient

Calibration:

After the operator is satisfied that there are no air bubbles in the tubes and that the calibration level is correct, calibration can begin. This is also an automated process where the solenoid pinch valves 21 are set so that pressure sensor 23 and 24 are connected to the pressure calibration tube 22. The pressure then is then zeroed to the level in the pressure calibration tube 22. The tube-set is constructed so that the level corresponds to a laser line emitted from the instrument. That line can in turn be used later to ensure that the instrument's zero pressure is in level with the patient's spine, while horizontal. The pressure calibration tube 22 is then used to check that the flow of the pump is calibrated correctly. The instrument does this by pumping liquid up the pressure calibration tube 22 during a preset time, and comparing the measured pressure difference to an expected pressure.

The preparations can be considered complete once these tests are passed, and the patient can be connected.

Investigation:

A patient can be in the ward or outpatient setting, sitting in a chair or a bed with a hole to allow for access to the patient's back. Two needles are placed between the L3/L4 spaces to allow for contact with the CSF. CELDA™ tool's two long tubes, patient IP tube 3 and Patient ICP tube 4, are unwound and connected to the needles in the spinal canal. The patient is placed in the horizontal position and the instrument's height is adjusted to set the zero level. The operator is then prompted to choose between different investigation protocols. For all protocols the solenoid pinch valves 21 are automatically set to the right position and pressure is measured using the pressure sensor 23, 24 integrated in CELDA™ tools. Pressure sensor 24 translates the fluid pressure information to electronic signals. Resting pressure is measured. An automatic infusion of artificial CSF is begun, and the solenoid pinch valves 21 automatically direct the fluid going through the tube-set. The pressure of the patient usually increases higher than normal, and in approximately ten minutes, absorption occurs and the pressure returns to baseline.

Results can be measured after 20-50 minutes, depending on the protocol. Three ways of measuring the results include constant pressure, constant flow, or injection bolus. The last way includes that the operator selects a volume of Ringer's acetate, which is infused by the pump at maximum rate. The preset volumes to choose from are 1, 2, 3, 4 or 5 mL. ICP will automatically return towards the resting pressure level once the infusion has ceased. The protocol will conclude automatically after 5 minutes.

Removal:

The tube-set comes packed with a slide clamp 17 to close off the pump tube 7 when removing the Ringer's acetate bag. The pressure calibration tube 22 is fitted with a porous plug 18 that prevents liquid from leaking out if the tube-set is turned upside down for a moment while disposing of it.

Example 4

The Different Phases of the Automatic System of the Invention

Figure 3:
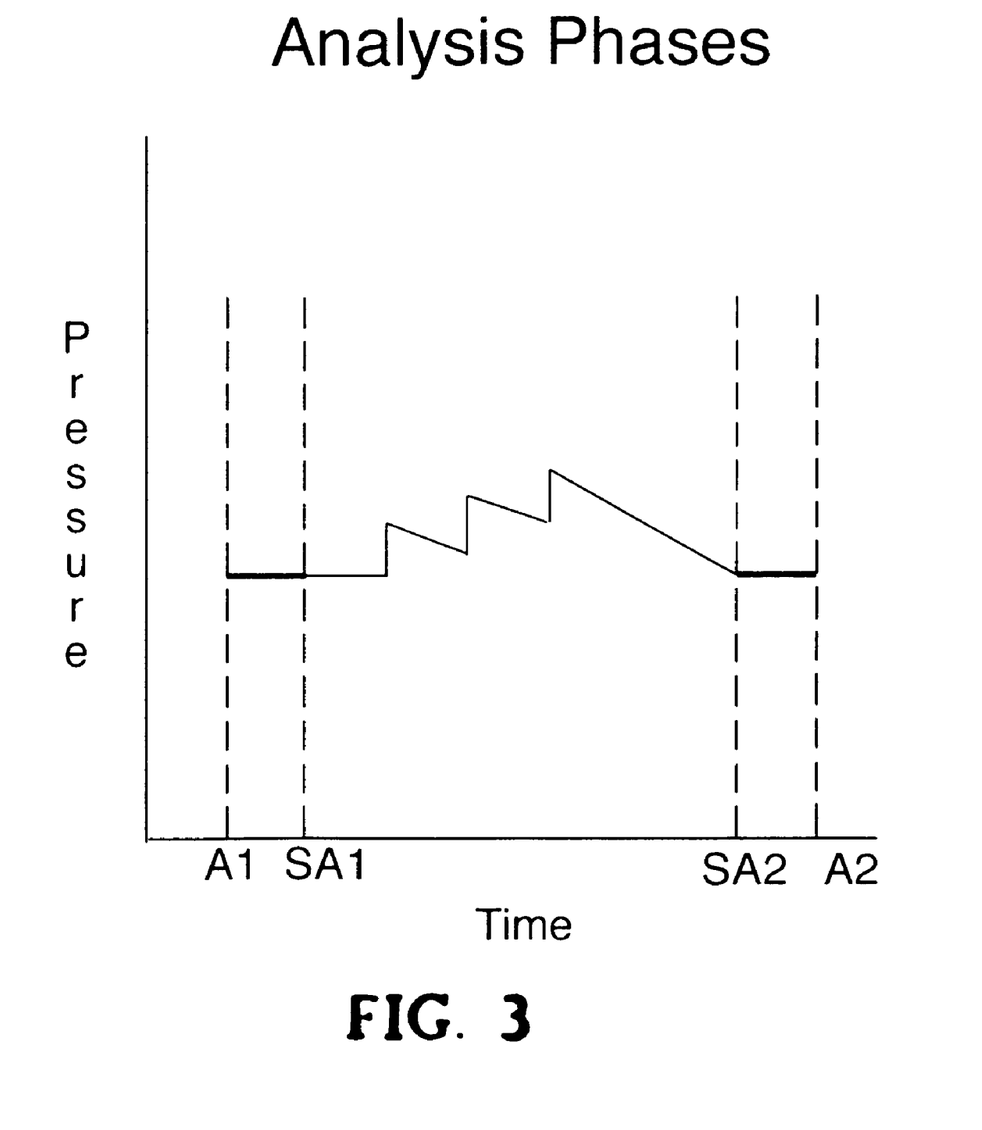
FIG. 3 is a graph showing the relation of pressure versus time of an example of automatic use of the invention herein.
Figure 4:
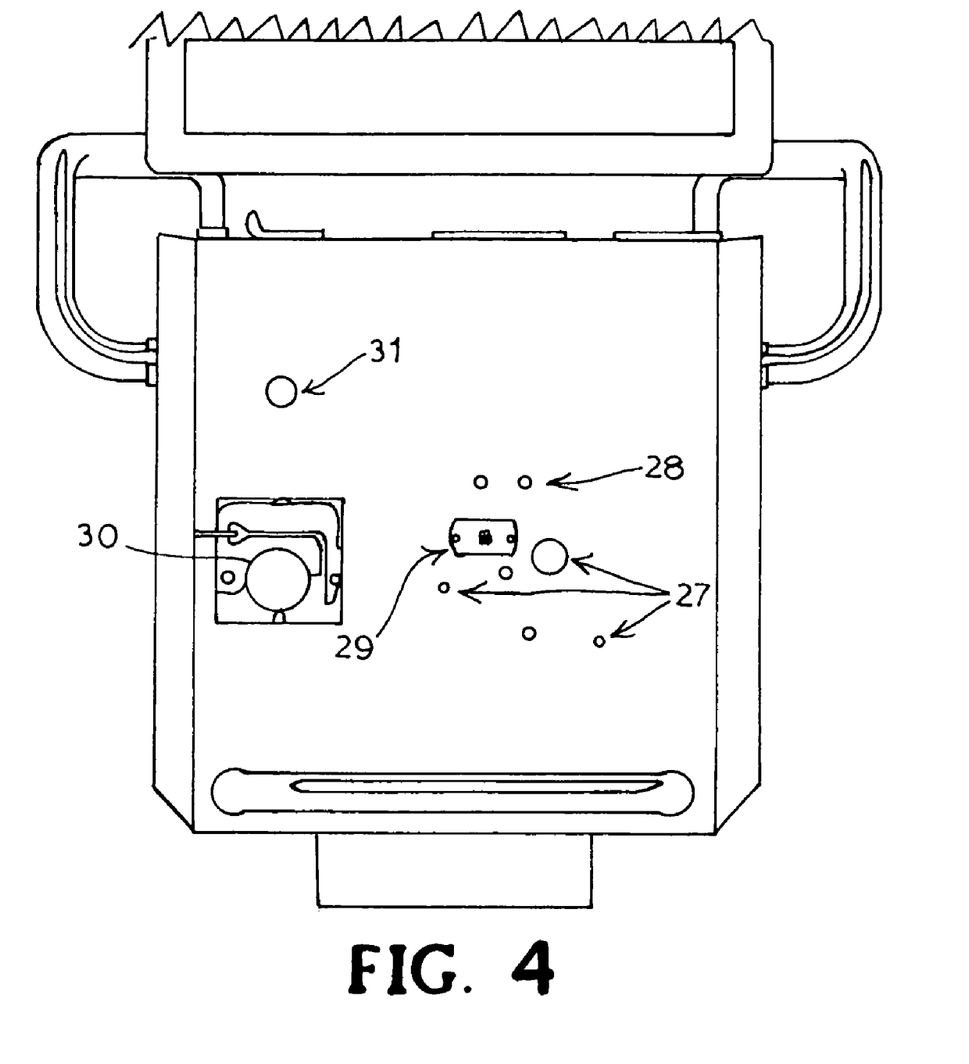
FIG. 4 show the instrument panel where the tube-set plate is fixed

FIG. 3 is a schematic graph representing the process and depicting that all phases of the invention herein regulating and measuring CSF parameters are automatically controlled. The graph shows the relation of pressure to time. A1-A2 shows that the investigation time is automatically controlled from the beginning of the process until the end of the process. A1-SA1 is the automatic filling and opening phases of valves. SA1-SA2 is the regulation phase of the CSF flow and measurement, as used in previous semi-automatic systems. SA2-A2 is the automatic closure of valves, which concludes the examination.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A device for measuring and regulating fluid parameters of cerebrospinal fluid in a patient's spinal canal, for use with an instrument having a housing and a pump and that systematically provides pressure and flow information, the device comprising:
   a) a disposable tube-set attachable to the instrument housing, comprising a disposable single-use tube-set plate, a plurality of tubes including a pressure calibration tube, and computer regulated automatic magnetic solenoid pinch valves to control fluid flow pressure;
   b) a small pressure sensor located on the tube-set which provides cerebrospinal fluid pressure information; and
   c) a pressure sensor for translating the fluid pressure information to electronic signals;
wherein the automatic magnetic solenoid pinch valves automatically open and close in response to the electronic signals, and control fluid flow and yield a measurement of patient results.

2. The device of claim 1, wherein the disposable tube-set is attachable to the instrument by clipping the tube-set on to the instrument using a central conical bayonet fitting.

3. The device of claim 1, wherein the tube-set further comprises a pump tube, and the plurality of tubes further comprises linking tubes, patient tubes and a liquid container at the distal ends of the patient tubes.

4. The device of claim 1, wherein the tube-set plate is made of polycarbonate.

5. The device of claim 1, wherein the device automatically adjusts fluid flow to the patient from the beginning to the end of patient examination.

6. The device of claim 1, wherein the location of the pressure sensor on the tube-set obviates needing to draw fluid into the instrument and improves sterility of patient examination.

7. The device of claim 1, wherein the device gives numerical feedback to a user concerning the reliability of individual patient investigations.

8. A method for measuring and regulating pressure and flow of cerebrospinal fluid in a patient's spinal canal, comprising:
   a) providing a device according to claim 1;
   b) clipping the tube-set on to the instrument;
   c) starting the instrument, which undergoes a self-test procedure, and then automatically primes the tube-set to fill the tubes of the tube-set with artificial cerebrospinal fluid;
   d) running the pump continuously;
   e) regulating the solenoid pinch valves to direct fluid flow to the tubes, which fill one by one;
   f) pumping the liquid to a specific level in the pressure calibration tube;

g) adjusting the instrument and tube-set as needed to remove any residual air bubbles or to finely adjust the level in the pressure calibration tube;

h) automatically calibrating by setting the solenoid pinch valves so that the pressure sensor is connected to the pressure calibration tube, and setting the pressure to the level in the calibration tube;

i) using the pressure calibration tube to check that the flow of the pump is calibrated correctly;

j) connecting tubes from the tube-set to the patient;

k) choosing an investigation protocol;

l) automatically setting the solenoid pinch valves for the chosen investigation protocol, and measuring pressure using the small pressure sensor;

m) beginning automatic infusion of artificial cerebrospinal fluid, with the solenoid pinch valves automatically directing the fluid through the tube-set; and n) measuring patient cerebrospinal fluid pressure and flow parameters during the patient investigation.

9. The method of claim 8, wherein results of the patient investigation are evaluated by a parameter selected from the group consisting of constant pressure, constant flow, and injection bolus.

10. The method of claim 8, wherein the calibration of the flow of the pump is checked by having the liquid pumped up the pressure calibration tube during a preset time, and comparing the measured pressure difference to an expected pressure.

11. The method of claim 8, wherein the tube-set is clipped to the instrument using a central conical bayonet fitting.

* * * * *